(12) United States Patent
Weigand

(10) Patent No.: US 12,288,125 B2
(45) Date of Patent: Apr. 29, 2025

(54) COMPONENT ARRANGEMENT FOR AN X-RAY THERAPY COMPONENT, X-RAY THERAPY SYSTEM, AND METHOD FOR OPERATING AN X-RAY THERAPY SYSTEM

(71) Applicant: Carl Zeiss Meditec AG, Jena (DE)

(72) Inventor: Frank Weigand, Heidenheim (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/651,204

(22) Filed: Apr. 30, 2024

(65) Prior Publication Data

US 2024/0281627 A1 Aug. 22, 2024

Related U.S. Application Data

(63) Continuation of application No. PCT/EP2022/081833, filed on Nov. 14, 2022.

(30) Foreign Application Priority Data

Nov. 15, 2021 (DE) ...................... 10 2021 212 808.4

(51) Int. Cl.
*G06K 7/10* (2006.01)
*A61N 5/10* (2006.01)

(52) U.S. Cl.
CPC ....... *G06K 7/10475* (2013.01); *A61N 5/1048* (2013.01); *A61N 5/1083* (2013.01)

(58) Field of Classification Search
CPC . G06K 7/10475; A61N 5/1048; A61N 5/1083
(Continued)

(56) References Cited

U.S. PATENT DOCUMENTS

2008/0296373 A1 12/2008 Zmood et al.
2009/0102612 A1 4/2009 Dalbow et al.
(Continued)

FOREIGN PATENT DOCUMENTS

CN 109561942 A 4/2019
CN 113440737 A 9/2021
(Continued)

OTHER PUBLICATIONS

International Preliminary Report on Patentability dated Oct. 4, 2023, of international patent application PCT/EP2022/081833 on which this application is based, and English language translation thereof.

(Continued)

*Primary Examiner* — Daniel A Hess
(74) *Attorney, Agent, or Firm* — Ewers IP Law PLLC; Falk Ewers

(57) ABSTRACT

A component arrangement includes an x-ray therapy component having a first RFID transponder, a primary packaging, in which the component is sterilely packed, and secondary packaging with a second RFID transponder in which the component packed in the primary packaging is arranged. An x-ray therapy system and a method for operating an x-ray therapy system are provided, in which data of a second RFID transponder arranged in and/or on secondary packaging of the component are read with a second RFID reader of a control device of the x-ray therapy system, and/or data are written to the second RFID transponder, the component sterilely packed in primary packaging is removed from the primary packaging, and data of a first RFID transponder of the component are read with a first RFID reader of an x-ray therapy device of the x-ray therapy system, and/or data are written to the first RFID transponder.

12 Claims, 2 Drawing Sheets

(58) Field of Classification Search
USPC .......................................................... 235/451
See application file for complete search history.

(56) References Cited

U.S. PATENT DOCUMENTS

| | | |
|---|---|---|
| 2014/0125482 A1 | 5/2014 | Rigsby et al. |
| 2014/0251845 A1 | 9/2014 | Roesler |
| 2016/0048712 A1 | 2/2016 | Butler et al. |
| 2016/0287901 A1 | 10/2016 | Dumaine et al. |
| 2019/0290392 A1 | 9/2019 | Hansen et al. |
| 2021/0084700 A1 | 3/2021 | Daniels |
| 2021/0299468 A1 | 9/2021 | Symalla et al. |

FOREIGN PATENT DOCUMENTS

| | | |
|---|---|---|
| DE | 10352556 A1 | 6/2005 |
| DE | 102013004168 A1 | 9/2014 |
| DE | 102020104628 B3 | 7/2021 |
| EP | 3868441 B1 | 12/2022 |
| WO | 2009052048 A1 | 4/2009 |
| WO | 2014071337 A1 | 5/2014 |
| WO | 2015066814 A1 | 5/2015 |

OTHER PUBLICATIONS

International Search Report and Written Opinion dated Feb. 17, 2023, of international patent application PCT/EP2022/081833 on which this application is based, and English language translation thereof.

Office Action dated Jul. 25, 2024 issued in Chinese counterpart application No. 202280071915.4, and English language translation thereof.

Chinese Search Report dated Jul. 23, 2024, of the Chinese counterpart application No. 202280071915.4, and English language translation thereof.

Chinese Office Action and Search Report dated Jan. 17, 2025, of the Chinese counterpart application No. 202280071915.4, and English language translation thereof.

COMPONENT ARRANGEMENT FOR AN X-RAY THERAPY COMPONENT, X-RAY THERAPY SYSTEM, AND METHOD FOR OPERATING AN X-RAY THERAPY SYSTEM

CROSS REFERENCE TO RELATED APPLICATIONS

This application is a continuation application of international patent application PCT/EP2022/081833, filed Nov. 14, 2022, designating the United States, claiming priority to German application 10 2021 212 808.4, filed Nov. 15, 2021, and the entire content of both applications is incorporated herein by reference.

TECHNICAL FIELD

The disclosure relates to a component arrangement for an x-ray therapy component, to an x-ray therapy system, and to a method for operating an x-ray therapy system.

BACKGROUND

With regards to components used in the field of x-ray therapy, it is important to know whether the components have already been used, since multiple use, e.g., in different systems and/or at different locations, may lead to a risk for the patient. In general, components made of plastic have only limited tolerance in relation to ionizing radiation, i.e., the components may lose assured properties when the applied dose is exceeded. Further, components with given properties must be provided within the scope of treatment planning and treatment preparation. The practice of marking medical components with the aid of radiofrequency identification (RFID) transponders (RFID tags) to allow these to be identified uniquely is known.

WO 2009/052048 A describes a system and a method for providing radiotherapy for a patient. The system includes at least one component provided with an RFID tag, for example a patient positioning apparatus used when the patient is intended to be subjected to a radiotherapy treatment. The at least one component is selected specifically for the use on the patient. The RFID tag contains patient-relevant information. The RFID tag is queried by a reader in order to create a signal used by an associated computer system in order to verify the position and presence of the patient and the components in the room in which the treatment is intended to be performed. The system and the method allow determination of the location of each patient, the selected institution staff and all components for the treatment of a specific patient. Moreover, the system and the method allow determination of the time spent by the patient and/or the staff and/or the component at a given location for a specific treatment.

WO 2014/071337 A1 describes systems and methods for marking and tracking surgical equipment using radiofrequency identification (RFID) tags. In general, the systems and methods allow surgical equipment to be tracked during the entire distribution and sterilization of same. In one example, the system includes an instrument tray which is configured to receive a plurality of pieces of surgical equipment and which has attached thereon a superordinate RFID tag which contains information and/or allows access to information about the tray and each piece of surgical equipment placed thereon. Each piece of surgical equipment located in the instrument tray can have attached a subordinate RFID tag which contains information and/or allows access to information about the piece of surgical equipment.

DE 10 2020 104 628 B3 describes an applicator for intraoperative radiotherapy. The applicator includes a receptacle for accommodating an irradiation probe and an insertion opening for inserting the irradiation probe into the receptacle. The insertion opening is sealed by a seal. Moreover, a first machine-readable information storage unit is present, the latter being at least partially arranged at the seal in such a way that a removal or destruction of the seal removes the readability of the information storage unit.

Within the scope of x-ray therapy, there are only unsatisfactory solutions to the problem of handling sterile components (for example applicators) in nonsterile areas within the scope of treatment planning and treatment preparation.

SUMMARY

It is an object of the disclosure to improve a handling of sterile components from x-ray therapy for treatment planning and treatment preparation.

The object is achieved by a component arrangement for an x-ray therapy component, an x-ray therapy system, and a method for operating an x-ray therapy system, as described herein.

One of the basic ideas of the disclosure is that of arranging a (second) RFID transponder in or on a nonsterile secondary packaging in addition to a (first) RFID transponder (which may also be referred to as RFID tag) arranged on or in a sterile component. The sterile component is situated within a primary packaging. In that case, the primary packaging and the sterile component can be moved independently of the secondary packaging and handled within the scope of treatment planning and preparation. In particular, in the state as supplied by the manufacturer, provision is made for the sterile component to be arranged in the primary packaging and the primary packaging to be arranged in the nonsterile secondary packaging. For treatment planning, the (second) RFID transponder on the secondary packaging can be read with a (second) RFID reader. This is implemented at an operating device of an x-ray therapy system which is situated, in particular, in a nonsterile area of an operating theater. Problems with sterility do not arise since the component continues to remain packaged sterilely in the primary packaging. The treatment planning is carried out at the operating device, for example by a medical physicist or any other specialist. The primary packaging can subsequently be taken from the secondary packaging and the sterile component is moved to a sterile area of the operating theater. There, the (first) RFID transponder arranged on or in the component is read with a (first) RFID reader arranged on an x-ray therapy device of the x-ray therapy system, for example to prompt clearance of the x-ray source or x-ray radiation and/or to lift a blocked state of the x-ray source or x-ray radiation.

In particular, a component arrangement for an x-ray therapy component is provided, including an x-ray therapy component which has a first RFID transponder, a primary packaging in which the component is packaged sterilely, and a secondary packaging which has a second RFID transponder arranged therein and/or thereon and in which the component packaged in the primary packaging is arranged.

Further, an x-ray therapy system is provided, including an x-ray therapy device having a holding device configured to hold and/or position at least one component in and/or on a patient, an operating device configured to control the x-ray therapy device, wherein the x-ray therapy device includes at least one first RFID reader configured to read-out data from a first RFID transponder arranged on or in the at least one component and/or write data to said first RFID transponder, and wherein the operating device includes at least one second RFID reader configured to read-out data from a second RFID transponder arranged in and/or on a secondary packaging and/or write data to said second RFID transponder.

Further, a method for operating an x-ray therapy system is provided, wherein configuring the x-ray therapy system for each of at least one component includes: a second RFID reader of an operating device of the x-ray therapy system being used to read data from a second RFID transponder arranged in and/or on a secondary packaging of the component and/or data being written to the second RFID transponder, the component sterilely packaged in a primary packaging being taken from the primary packaging, and a first RFID reader of an x-ray therapy device of the x-ray therapy system being used to read data from a first RFID transponder of the component and/or data being written to the first RFID transponder.

The component arrangement, the x-ray therapy system, and the method allow improved handling of x-ray therapy components within the scope of treatment planning and treatment preparation. The use of two RFID transponders on or in a secondary packaging and on or in the component also solves the problem of it generally not being possible to read out the RFID transponder arranged on or in the component when the component is in the packaged state since a distance between the RFID transponder and an RFID reader is too large under the given circumstances. Further, the secondary packaging can be spatially separated from the primary packaging and the sterile component such that treatment planning and/or a treatment preparation can be performed without the sterile component itself on the (nonsterile) operating device of the x-ray therapy system.

In particular, the component is an x-ray therapy component. For example, the component might be an applicator which is arranged on an x-ray source during a treatment, and which serves for targeted administration and shielding of x-ray radiation.

The operating device itself is formed separately from the x-ray therapy device. However, the operating device and the x-ray therapy device are signal connected to one another. In particular, the operating device includes a control device for controlling a treatment of the patient using the x-ray therapy device. The data read out from the second RFID transponder are evaluated in the operating device, especially with the control device, for the purpose of treatment planning. In particular, configuration parameter for the x-ray therapy device can be created here using the read-out data as a starting point.

The data read from and/or written to the RFID transponders may for example include the following data: a use state (e.g., used/unused/sterile), a number of uses, a date and a time of a performed operation, an applied dose in Gy/min, a name of a hospital, a name of the surgeon, a name of the medical physicist, etc.

Parts of the operating device and/or x-ray therapy device, in particular one or more control devices, may be configured, either individually or together, as a combination of hardware and software, for example as program code that is executed on a microcontroller or microprocessor. However, provision may also be made for parts to be configured, either individually or together, as application-specific integrated circuits (ASICs) and/or field-programmable gate arrays (FPGAs).

The x-ray therapy device includes a holding device which is formed as a stand or includes a stand, for example. In principle, however, the holding device may have a different embodiment and for example may be formed as a holding arm or may include a holding arm. For example, such a holding arm can be arranged at a patient's bed. Further, the x-ray therapy device includes an x-ray source arranged on the holding device, in particular at a (distal) end of a stand or holding arm. An (x-ray) applicator can be arranged on the x-ray source as a component. Before a treatment is performed with x-ray radiation from the x-ray source, it is established, whether the first RFID transponder of a component envisaged for the treatment, for example of an applicator arranged on the x-ray source, is registered by the first RFID reader. In principle, the presence of further given components, for example a holding plate, etc., can be monitored and/or verified. Clearance for the treatment, for example given by clearing the x-ray source using a clearance signal or by lifting a blocking signal, is given only if the presence of the component was detected. Together, the first RFID transponder and the first RFID reader form an interlock, in particular, which is used to monitor and secure an operation of the x-ray source.

A primary packaging is a welded sleeve (peel pouch) or a blister pack sealed using a sterile barrier (e.g., Tyvek® seal), in which pouch or blister pack the sterile component is arranged.

A secondary packaging is a non-sterile packaging made of cardboard and/or paperboard. In particular, the secondary packaging is in the form of a box or collapsible box. For example, the second RFID transponder is arranged in the form of a label on an inner side or an outer side of the secondary packaging, for example adhesively bonded thereon. A primary packaging arranged inside of the secondary packaging contains only one component. Expressed differently, each component is assigned a primary packaging and a secondary packaging.

An exemplary embodiment provides for the first RFID transponder and/or the second RFID transponder to provide unique component identification data. This can be a unique serial number, in particular a UID (unique identifier). A component can be identified unambiguously as a result. The unique component identification data are stored in a memory of the respective RFID transponder and can be retrieved therefrom with an RFID reader. For example, further information regarding the at least one component can be retrieved from a database by way of the unique component identification data.

An exemplary embodiment provides for the first RFID transponder to be biocompatible. As a result, the first RFID transponder can come into contact with tissue of the patient without this leading to impairments. To this end, the first RFID transponder is for example embedded in glass or a suitable plastic.

An exemplary embodiment provides for the first RFID transponder to be sterilizable with a sterilization method. As a result, the component with the first RFID transponder can be re-sterilized after one use and used again as a result. For example, the sterilization method may include steam sterilization and/or gamma irradiation.

RFID transponders which may be used are listed by way of example in the table below:

| Manufacturer | Model | Frequency | Memory | Application location | Encapsulation | Sterilizability |
| --- | --- | --- | --- | --- | --- | --- |
| HIDGlobal | 6B0201 | 13.56 MHz | 1664 bits | Glass, metal, plastic, wood | Glass tube | Steam |
| HIDGlobal | In Tag 200 | 13.56 MHz | 16 kbit | Glass, plastic, wood | Plastic | Gamma |
| HIDGlobal | Piccolino Tag 634190 | 13.56 MHz | 16 kbit | NS | Epoxy resin | Steam |
| Neosid | 704032 | 13.56 MHz | 896 bits | Non-metallic objects | Plastic | Steam |
| Neosid | 704033 | 13.56 MHz | 896 bits | Metallic objects | Plastic | Steam |
| Xerafy | Dot-iN XS | 866-868 MHz | 512 bits | Glass | Ceramic | Steam |
| Xerafy | Pico-iN Plus | 866-868 MHz | 512 bits | NS | Ceramic | Steam |
| Xerafy | Dash-iN XS | 866-868 MHz | 512 bits | Glass, metal, plastic, wood | Ceramic | Steam |

An exemplary embodiment provides for the component to be an applicator for x-ray therapy. The applicator is arranged for use at or on an x-ray source of the x-ray therapy system. In particular, the applicator serves to arrange tissue to be irradiated at a given distance from an initial point (i.e., from the target) of the x-ray radiation and to protect tissue not to be irradiated.

An exemplary embodiment provides for the at least one first RFID reader to be arranged on the holding device, for example on a stand, in a connection region in which, for use purposes, the at least one component is arranged or can be arranged on the holding device. This allows a communications link to the first RFID transponder to be established, especially also in the case of the limited transmission power of the first RFID reader. The arrangement of the first RFID reader and the restriction of the transmission power of the first RFID reader can ensure that the component is only registered if it is arranged in the connection region. In particular, this allows the provision of an interlock in which the x-ray source and an x-ray radiation are only cleared if a specified component (or a plurality of specified components) is/are arranged in the connection region. For example, provision can be made for the x-ray source to be cleared for operation only if an applicator is arranged on the x-ray source. In that case, the connection region and a transmission power of the first RFID reader are chosen such that a distance between the first RFID transponder and the first RFID reader is only small enough to allow establishment of a communications link therebetween and to allow the data to be read from the first RFID transponder if the applicator is arranged on the x-ray source in the region of the connection region.

An exemplary embodiment provides for clearance to be given to the x-ray therapy if the data from the first RFID transponder of the at least one component includes at least one piece of specified information. This can ensure that the at least one component has specified properties (e.g., use state, number of uses, specified type). A maloperation and/or an incorrect use can be avoided as a result. For example, provision can be made for a use of the x-ray therapy device to be prevented if it is established post readout of the first RFID transponder that at least one piece of information is not present. For example, the at least one piece of information may include a serial number and/or a type number, in particular a UID (unique identifier). For example, prior to the use of a component, it is possible to verify whether the component has already been used (use state) by virtue of reading out and verifying the corresponding piece of information. Accordingly, a piece of information stating that the component has already been used (or is unused) can be stored in the memory of the first RFID transponder following each use (cf. the exemplary embodiment described below). Further, it is for example possible to verify whether a maximum number of uses has already been reached (number of uses). To this end, following readout, a number of uses stored in a memory of the first RFID transponder can be compared with a maximum value. Taking account of a comparison result, a clearance signal for the x-ray source and/or the treatment is or is not created.

An exemplary embodiment provides for a use of the at least one component to be followed by storing a piece of information in the first RFID transponder, the information marking the at least one component as used and/or including a number of uses of the at least one component. In this way, the at least one component can be labeled directly as used. Then, prior to the use of a component, it is possible to verify whether the component has already been used by virtue of reading out and verifying the corresponding piece of information. Further, it is for example possible to verify whether a maximum number of uses has already been reached. To this end, following readout, the number of uses can be compared with a maximum value, for example. Taking account of a comparison result, a clearance signal for the x-ray source and/or the treatment is or is not created.

An exemplary embodiment provides for the first RFID transponder to be rendered unusable after use and/or once a given number of uses have been reached. The first RFID transponder can be irreversibly marked in this way. This can limit a number of uses of the component overall. For example, this is required once a material of the component, for example a plastic, has reached a maximally admissible overall dose of ionizing radiation. For example, irreversible destruction can be implemented by creating a transmission pulse of a given power above a suitable threshold value, said transmission pulse leading to a thermal destruction (severing and/or short-circuiting) of conductor tracks in the first RFID transponder on account of an overall amount of coupled-in energy. Subsequently, the first RFID transponder no longer works and can no longer be read.

An exemplary embodiment provides for the at least one component to be sterilized after one use. In this way, the at least one component can be reused. In this case, the first RFID transponder has a sterilizable embodiment and undergoes sterilization together with the component. For example, the component and the first RFID transponder can be arranged in a sterilization tray (or instrument tray) or in a peel pouch and can subsequently undergo a sterilization method (e.g., steam sterilization or gamma ray sterilization). Prior to arrangement in the sterilization tray or peel pouch, the component is reset to the "unused" state by appropriate writing to the first RFID transponder, for example by virtue of a bit provided to this end being changed. The secondary packaging remains outside of the tray or peel pouch, with the result that the second RFID transponder can still be read and/or written at the operating device for preparation and/or planning purposes. Provision can be made for the component to be stored in the nonsterile state in the secondary packaging after one use and subsequent cleaning and to be sterilized only when required again. However, in principle, the procedure in this case is as described above. In particular, the component is marked as "unused" only just before it is arranged in the tray or peel pouch.

BRIEF DESCRIPTION OF THE DRAWINGS

The invention will now be described with reference to the drawings wherein.

DESCRIPTION OF EXEMPLARY EMBODIMENTS

Figure 1:
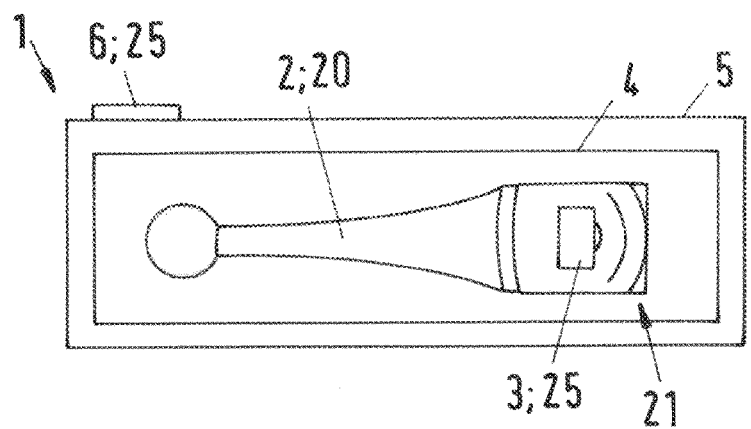
FIG. 1 shows a schematic illustration of the component arrangement for an x-ray therapy component according to an exemplary embodiment of the disclosure.

FIG. 1 shows a schematic illustration of an exemplary embodiment of the component arrangement 1 for an x-ray therapy component 2.

The component arrangement 1 includes an x-ray therapy component 2 which has a first RFID transponder 3. The first RFID transponder 3 is arranged in or on the component 2. In particular, the component 2 is configured as an applicator 20 which can be connected to an x-ray source in a connection region 21 (cf. FIG. 2). In particular, the first RFID transponder 3 is arranged in the connection region 21 or in the proximity of the connection region 21 such that the first RFID transponder 3 can be read out and/or written to by an RFID reader arranged on the x-ray source.

The component arrangement 1 also includes a primary packaging 4 in which the component 2 is packaged sterilely. For example, the primary packaging 4 can be a peel pouch or a blister pack sealed with a sterile barrier (e.g., Tyvek® film).

Further, the component arrangement 1 includes secondary packaging 5 with a second RFID transponder 6 arranged therein and/or thereon. The primary packaging 4 and the component packaged sterilely therein are arranged in the secondary packaging 5. For example, the secondary packaging 5 is in the form of a box or collapsible box made of paperboard or cardboard. The secondary packaging 5 is nonsterile and serves to handle, provide transport protection for, and store the sterile component 2 in the primary packaging 4.

Provision can be made for the first RFID transponder 3 and/or the second RFID transponder 6 to provide unique component identification data 25. The unique component identification data 25 include a unique serial number (e.g., a unique identifier, UID). In this case, the unique component identification data 25 are stored in a memory of the RFID transponder 3, 6 and can be retrieved therefrom and rendered available when required.

Provision can be made for the first RFID transponder 3 to be biocompatible. This allows contact between the first RFID transponder 3 and biological tissue. To this end, the RFID transponder 3 can be encapsulated in a (bio)glass or a suitable plastic, for example.

Provision can be made for the first RFID transponder 3 to be sterilizable with a sterilization method. RFID transponders 3 suitable to this end were already presented above.

Figure 2:
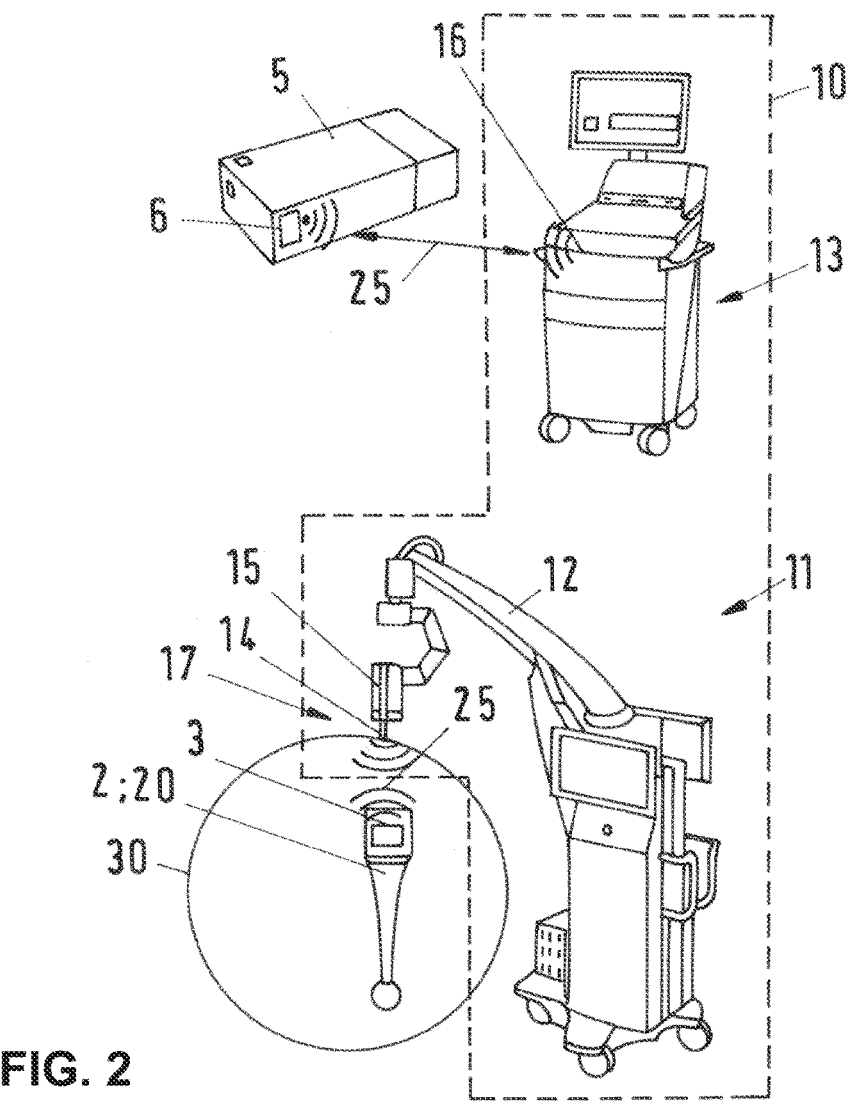
FIG. 2 shows a schematic illustration of the x-ray therapy system according to an exemplary embodiment of the disclosure.

FIG. 2 shows a schematic illustration of an exemplary embodiment of the x-ray therapy system 10. The x-ray therapy system 10 includes an x-ray therapy device 11 having a holding device 12 which is configured to hold and/or position at least one component 2 in and/or on a patient. For example, the holding device 12 is in the form of a stand or includes a stand. The x-ray therapy system 10 also includes an operating device 13 which is configured to control the x-ray therapy device 11.

At least one portion of the holding device 12, in particular the portion on which the at least one component 2 is or can be arranged, is located in a sterile region 30 of the operating theater. The remaining x-ray therapy system 10, especially the operating device 13, is situated outside of the sterile region 30 in a nonsterile region and can accordingly be managed more easily.

The x-ray therapy device 11 includes a first RFID reader 14 configured to read-out data from a first RFID transponder 3 arranged on or in the at least one component 2 and/or write data to said first RFID transponder. In particular, provision is made for the at least one first RFID reader 14 to be arranged on the holding device 12 in a connection region 17 in which, for use purposes, the at least one component 2 is arranged or can be arranged on the holding device 12. In particular, the RFID transponder 3 is arranged in a connection region 17 in which the component 2, in particular an applicator 20, is arranged or can be arranged on an x-ray source 15 arranged on the holding device 12.

The operating device 13 includes a second RFID reader 16 configured to read-out data from a second RFID transponder 6 arranged in and/or on a secondary packaging 5 and/or write data to said second RFID transponder.

Both the x-ray therapy device 11 and the operating device 13 includes respective control devices (not shown), each with a computing device and a memory. For example, the computing devices each include a microprocessor and are configured to execute program code stored in the memory. In particular, the control devices are configured to control communication between the respective RFID readers 14, 16 and RFID transponders 3, 6 and to read-out and evaluate data, in particular unique component identification data 25, from the respective RFID transponders 3, 6 and/or to write data to said RFID transponders. In particular, the control device of the x-ray therapy device 11 provides a functionality of an interlock in this manner, with the result that the x-ray therapy device 11 can only be operated or a treatment is only cleared if the at least one specified component 2 is arranged correctly and unused (sterile). In particular, this can ensure that an (unused/sterile) applicator 20 is arranged on the x-ray source 15 before the x-ray source 15 is activated. Further, provision can be made for a functionality of other components of the x-ray therapy device 11, for example the holding device 12 for holding the x-ray source 15 and the applicator 20, to also be blocked or cleared depending on a presence of the applicator 20 on the x-ray source 15. This can prevent the arrangement of the used/nonsterile applicator 20 on or in the patient.

Figure 3:
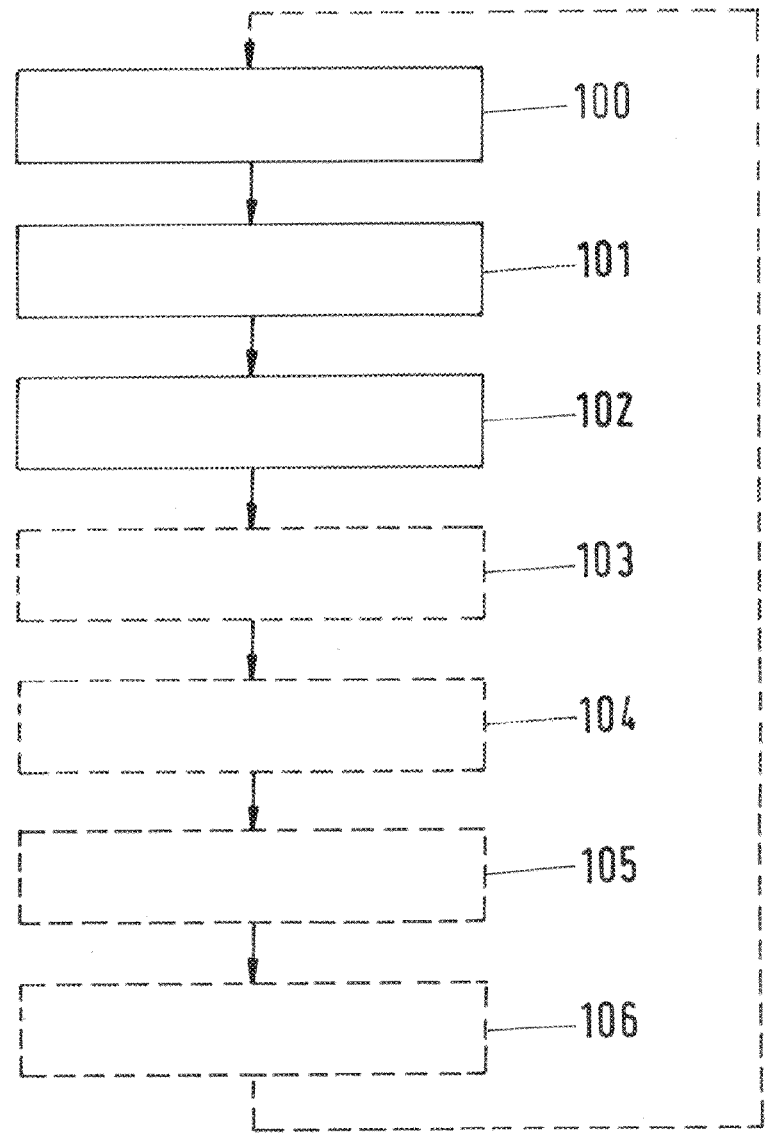
FIG. 3 shows a schematic flowchart of the method for operating an x-ray therapy system according to an exemplary embodiment of the disclosure.

FIG. 3 shows a schematic flowchart of the method for operating an x-ray therapy system 10 according to an exemplary embodiment of the disclosure. In addition to FIG. 3, reference is also made to FIG. 2 hereinafter.

To set up the x-ray therapy system 10, the steps described below are carried out for each of at least one component 2. The steps are only described for one component 2 herein. However, in principle, the method can be implemented in the same way for further components 2 as well. In particular, the component 2 is an applicator 20 which is arranged on the x-ray source 15 of the x-ray therapy device 11 during the x-ray therapy.

In a step 100, the second RFID reader 16 of the operating device 13 of the x-ray therapy system 10 is used to read data from a second RFID transponder 6 arranged in and/or on a secondary packaging 5 of the component 2 and/or data are written to the second RFID transponder 6.

In particular, provision is made for unique component identification data 25 (e.g., a unique identifier, UID) to be read from the second RFID transponder in the process. A treatment can be prepared on the operating device 13 with the aid of the read-out data. For example, a type and properties of an applicator 20 for a treatment plan can be stored in the x-ray therapy system 10. In principle, a plurality of similar components 2 of different types (e.g., applicators with different shapes) can also be stored, and the used component 2 is selected therefrom just before the specific treatment (e.g., a shape of the applicator 20 is selected depending on the course of an operation).

In a step 101, the component 2 packaged sterilely in a primary packaging, in particular the applicator 20, is taken from the primary packaging. If the primary packaging is arranged in the secondary packaging 5, then the primary packaging is removed together with the component 2 arranged therein from the secondary packaging 5. In this case, the sterilely packaged component 2 is taken from the primary packaging in such a way that sterility of the component 2 is not lost in the process.

In a step 102, the first RFID reader 14 of the x-ray therapy device 11 of the x-ray therapy system 10 is used to read data from the first RFID transponder 3 of the component 2 of the applicator 20, and/or data are written to the first RFID transponder 3. In particular, provision is made for unique component identification data 25 (e.g., a unique identifier, UID) to be read from the first RFID transponder 3 in the process. Further, provision can be made for data to be read out in the process, said data including a piece of information as to whether the component 2 has already been used.

Provision can be made for the x-ray therapy to be cleared in a step 103 if the data of the first RFID transponder 3 of the component 2, in particular of the applicator 20, include at least one specified piece of information. In particular, provision is made for unique component identification data 25 (e.g., a unique identifier, UID) to be verified in the process. In an alternative or in addition, a blocking signal may be created if the data do not include the at least one specified piece of information. For example, the at least one specified piece of information may include a use state specifying that the component 2 must be unused. For example, a bit reserved accordingly to this end can be checked. The treatment is cleared if the bit contains the specified piece of information (unused), and not cleared otherwise.

A step 104 can provide for a use of the component 2, in particular the applicator 20, to be followed by storing a piece of information in the first RFID transponder 3, the information marking the component 2 as used and/or including a number of uses of the component 2. To this end, corresponding data are written to a memory of the first RFID transponder 3.

A step 105 can provide for the first RFID transponder 3 to be rendered unusable after use and/or once a given number of uses have been reached. For example, this is implemented by coupling-in a high transmission power (above a suitable threshold value) which irreversibly destroys and/or short circuits conductor tracks of the first RFID transponder 3 by thermal energy influx.

A step 106 can provide for the component 2, in particular the applicator 20, to be sterilized after one use. To this end, the component 2 is arranged in a sterilization tray or a peel pouch, for example. In this case, the sterilization tray or the peel pouch form a primary packaging, in particular, after the sterilization. In this case, provision is made in particular for the first RFID transponder 3 to be written with data immediately before the sterilization, said data including a piece of information marking the component 2 as unused and/or as a sterile. For example, a bit changed previously (i.e., after use) can be reset again. Subsequently, the steps described above can be implemented again with the sterilized component 2.

The method described in this disclosure improves handling of components in radiotherapy. In particular, this can facilitate preparation and work both in the nonsterile region and in the sterile region. This can improve, in particular facilitate, treatment planning and a treatment preparation. In particular, a workflow is improved since this enables fast and uncomplicated registration and/or writing of the data in relation to the at least one component independently of one another both in the nonsterile region and sterile region of an operating theater.

LIST OF REFERENCE NUMERALS

1 Component arrangement
2 Component
3 First RFID transponder
4 Primary packaging
5 Secondary packaging
6 Second RFID transponder
10 X-ray therapy system
11 X-ray therapy device
12 Holding device
13 Operating device
14 First RFID reader
15 X-ray source
16 Second RFID reader
17 Connecting region
20 Applicator
21 Connecting region
25 Component identification data
30 Sterile region
100-106 Steps of the method

What is claimed is:
1. A component arrangement for an x-ray therapy component, comprising:
an x-ray therapy component which has a first RFID transponder;
a primary packaging in which the x-ray therapy component is packaged sterilely;

a secondary packaging in which the x-ray therapy component packaged in the primary packaging is arranged; and a second RFID transponder arranged in and/or on the secondary packaging.

2. The component arrangement as claimed in claim 1, wherein at least one of (1) the first RFID transponder and (2) the second RFID transponder are configured to provide unique component identification data.

3. The component arrangement as claimed in claim 1, wherein the first RFID transponder is biocompatible.

4. The component arrangement as claimed in claim 1, wherein the first RFID transponder is sterilizable with a sterilization method.

5. The component arrangement as claimed in claim 1, wherein the x-ray therapy component is an applicator for x-ray therapy.

6. An x-ray therapy system, comprising:
an x-ray therapy device having a holding device configured to at least one of (1) hold and (2) position at least one x-ray therapy component of the component arrangement as claimed in claim 1 in and/or on a patient;
an operating device configured to control the x-ray therapy device,
wherein the x-ray therapy device includes at least one first RFID reader configured to at least one of (1) read-out data from the first RFID transponder arranged on or in the at least one x-ray therapy component of the component arrangement and (2) write data to the first RFID transponder,
wherein the operating device includes at least one second RFID reader configured to at least one of (1) read-out data from the second RFID transponder arranged in and/or on the secondary packaging of the component arrangement and (2) write data to said second RFID transponder, and
wherein the x-ray therapy system is configured, for each of at least one x-ray therapy component, to:
utilize a second RFID reader of an operating device of the x-ray therapy system to at least one of (1) read data from a second RFID transponder arranged in and/or on a secondary packaging of the at least one x-ray therapy component and (2) write data to the second RFID transponder,
take the at least one x-ray therapy component sterilely packaged in a primary packaging from the primary packaging, and
utilize a first RFID reader of an x-ray therapy device of the x-ray therapy system to at least one of (1) read data from a first RFID transponder of the at least one x-ray therapy component and (2) write data to the first RFID transponder.

7. The x-ray therapy system as claimed in claim 6, wherein the at least one first RFID reader is arranged on the holding device in a connection region in which the at least one x-ray therapy component is arranged or can be arranged on the holding device.

8. A method for operating an x-ray therapy system, the method comprising:
configuring the x-ray therapy system for each of at least one x-ray therapy component present in the component arrangement as claimed in claim 1 by:
utilizing a second RFID reader of an operating device of the x-ray therapy system to at least one of (1) read data from a second RFID transponder arranged in and/or on a secondary packaging of the at least one x-ray therapy component and (2) write data to the second RFID transponder;
taking the at least one x-ray therapy component sterilely packaged in a primary packaging from the primary packaging; and
utilizing a first RFID reader of an x-ray therapy device of the x-ray therapy system to at least one of (1) read data from a first RFID transponder of the at least one x-ray therapy component and (2) write data to the first RFID transponder.

9. The method as claimed in claim 8, further comprising:
giving clearance to an x-ray therapy if the data from the first RFID transponder of the at least one x-ray therapy component include at least one piece of specified information.

10. The method as claimed in claim 8, wherein a use of the at least one x-ray therapy component is followed by storing a piece of information in the first RFID transponder, and
wherein the information at least one of (1) marks the at least one x-ray therapy component as used and (2) includes a number of uses of the at least one x-ray therapy component.

11. The method as claimed in claim 8, wherein the first RFID transponder is rendered unusable after use and/or once a given number of uses have been reached.

12. The method as claimed in claim 8, wherein the at least one x-ray therapy component is sterilized after one use.

* * * * *